United States Patent [19]

Dowd et al.

[11] Patent Number: 4,968,620

[45] Date of Patent: Nov. 6, 1990

[54] BIOLOGICALLY PURE CULTURE OF YEAST STRAIN USED FOR THE MICROBIAL DETOXIFICATION OF XENOBIOTICS

[75] Inventors: Patrick F. Dowd; Samuel K. Shen, both of Peoria, Ill.

[73] Assignee: The United States of America, as represented by the Secretary of Agriculture, Washington, D.C.

[21] Appl. No.: 303,327

[22] Filed: Jan. 30, 1989

[51] Int. Cl.$^5$ .................. C12R 1/645; C12N 1/16; C12P 1/02

[52] U.S. Cl. .................. 435/255; 435/171; 435/911

[58] Field of Search .................. 435/911, 255

[56] References Cited

PUBLICATIONS

C.A. 16176 (1972) 97094p Jurzitza (Z. Vergl. Physiol) (1969, 63(2) 165–181).

C.A. vol. 109 (224237q) 1988, Ahlers et al., Chemosphere 1987 17(8) 1603–1615.

Anton Koch, "Intracellular Symbiosis in Insects", Annu. Rev. Microbiol. 14: 121–140 (1960).

M. Amiressami and H. Petzold, Symbioseforschung und Insektizidresistenz: Ein Licht- und elektronenmikroskopischer Beitrag zur Klarung der Insektizidresistenz von Aphiden unter Berucksichtigung der Mycetomsymbionten bei *Myzus persicae* Sulz. Zeitschr. f. angew. Ent. 82: 252–259 (1977).

M. Amiressami, "Investigation of the Light Microscopical and Ultrastructure of the Demeton-S-Methyl Resistance Aphids under Consideration of the Mycetome Symbients of the *Phorodon humuli* Schrank", In Endocytobiology Endosymbiosis and Cell Biology, W. Schwemmler and H. E. A. Schenk (eds.), vol. I, pp. 425–443 (1980).

C. G. Jones, "Microorganisms as Mediators of Plant Resource Exploitation by Insect Herbivores", In a New Ecology: Novel Approaches to Interactive Systems, P. W. Price et al. (eds.), John Wiley & Sons, New York, pp. 53–99 (1984).

J. P. van der Walt, "The Mycetome Symbiont of *Lasioderma serricorne*", Ant. v. Leu. 27: 362–366 (1961).

Gerhard Jurzitza, "Studien an der Symbiose der Anobiiden. II. Physiologische Studien am Symbionten von Lasioderma serricorne F.", Archiv. für Mikrobiologie 49: 331–340 (1964).

Max Levine et al., A Compilation of Culture Media for the Cultivation of Microorganisms, The Williams & Wilkins Company, Baltimore, p. 435 (1930).

*Primary Examiner*—Herbert J. Lilling
*Attorney, Agent, or Firm*—M. Howard Silverstein; John D. Fado; Curtis P. Ribando

[57] ABSTRACT

A strain of symbiotic yeast NRRL Y-18546 from the cigarette beetle (*Lasioderma serricorne*) has been discovered, which is capable of detoxifying a variety of zenobiotics including insecticides, herbicides, mycotoxins, and plant toxins (allelochemicals). Thus, compositions of the yeast provide a biological alternative to chemical detoxification of xenobiotics.

1 Claim, No Drawings

BIOLOGICALLY PURE CULTURE OF YEAST STRAIN USED FOR THE MICROBIAL DETOXIFICATION OF XENOBIOTICS

BACKGROUND OF THE INVENTION

1. Field of the Invention

The rapidly expanding use of pesticides throughout the world has been accompanied by increasing public apprehension about hazardous waste materials resulting from their use. Concern also exists with the presence in food of other xenobiotics such as mycotoxins and plant toxins (allelochemicals). This invention relates to a method of detoxifying xenobiotics by application of a symbiotic yeast from the cigarette beetle (*Lasioderma serricorne*).

2. Description of the Prior Art

The detoxifying capabilities of microorganisms are highly variable, depending on the microorganisms and the substrates involved. Several dozen different insecticides, representing all major classes, may be metabolized (and presumably detoxified) by microorganisms [Wallnofer et al., In Handbook of Microbiology, Volume VII, Microbial Transformation, A. Laskin et al. (ed.), CRC Press, Boca Raton, pp. 491–558 (1984)]. Likewise, a variety of plant allelochemicals may also be used as sole carbon sources [Gledhill, ibid., pp. 1–50].

Intracellular symbiotic microorganisms which are found in insects may produce amino acids, lipids, vitamins, or other nutrients for their hosts [Koch, Annu. Rev. Microbiol. 14: 121–140 (1960)]. However, the contribution of these symbionts appears to be more than nutritional; the cell enlargement of symbionts in insecticide-resistant aphids has caused speculation that the symbionts may contribute to the resistance through detoxification [Amiressami et al., Z. Ang. Entomol. 82: 252–259 (1977); Z. Ang. Zool. 63: 273–289 (1976); In Endocytobiology, Endosymbiosis and Cell Biology: A Synthesis of Recent Research, W. Schwemmler et al. (ed.), Walter de Gruyter, New York, pp. 425–443 (1980)]. The involvement of both intracellular and extracellular symbionts of herbivorous insects in detoxification of plant allelochemicals is postulated to be widespread [Jones, In A New Ecology: Novel Approaches to Interactive Systems, P. Price et al. (ed.), Wiley, New York, pp. 53–99 (1984)]. However, actual detoxification of any xenobiotics by intracellular symbionts has never been demonstrated.

SUMMARY OF THE INVENTION

We have now discovered a new strain of intracellular symbiotic yeast from the cigarette beetle (*L. serricorne*) that is capable of detoxifying a variety of xenobiotics.

In accordance with this discovery, it is an object of the invention to provide a new microorganism that can be artificially mass-produced and formulated for the detoxification of xenobiotics.

It is also an object of the invention to provide new compositions for detoxifying xenobiotics.

Another object of the invention is to provide a biological alternative to chemical detoxification of xenobiotics.

Other objects and advantages of this invention will become readily apparent from the ensuing description.

DETAILED DESCRIPTION OF THE INVENTION

The symbiotic yeast for use herein is a strain isolated from a starter culture of *L. serricorne* that was obtained from the USDA-ARS Stored Products Insects Research and Development Laboratory, Savannah, Ga. This strain, which can be cultured apart from the host, was found to be capable of metabolizing and/or modifying a wide variety of xenobiotics. The term "xenobiotics" as used herein is defined as unwanted toxins, regardless of source.

The morphology of the isolate is identical to that reported previously by van der Walt [Ant. V. Leu. 27: 362–366 (1961)]. However, the isolate can use nitrate, in contrast to strains reported by others [van der Walt, supra; Jurzitza, Arch. Mikrobiol. 49: 331–340 (1964)]. This isolate has been deposited under the Budapest treaty in the ARS Culture Collection (NRRL) in Peoria, Ill., under the name Symbiotaphrinasp and has been assigned Accession Number NRRL Y-18546. For purposes of this invention, any isolate of this yeast having the identifying characteristics of NRRL Y-18546, including subcultures thereof, would be effective.

The yeast can be mass-produced and maintained for use by any conventional means. The preferred temperature range for growth is about 25°–27° C., and the pH should be in the range of about 5–9, preferably about 7.4. The yeast is preferably incorporated into compositions appropriate for the desired applications by combining it with a suitable liquid vehicle or solid carrier. The actual concentration of NRRL Y-18546 in the formulated composition is not particularly critical and is a function of practical considerations such as the properties of the vehicle or carrier, the type of toxic substrate, and the method of application to substrate. For purposes of formulation and application, an "effective amount" is defined to mean any such quantity of NRRL Y-18546 sufficient to detoxify the target substrate.

While not desiring to be bound to any particular theory of operation, it has been demonstrated (see Examples 3 and 4) that detoxification of certain ester xenobiotics is effected by enzymatic (esterase) hydrolysis to less toxic derivatives. However, it is obvious from the results in Table I that non-ester xenobiotics are metabolized by NRRL Y-18546, indicating that mechanisms other than ester hydrolysis can also be involved. Unlike other detoxifying microorganisms, NRRL Y-18546 is effective against a much wider range of toxic compounds, including a variety of insecticides, herbicides, mycotoxins, and biologically active plant chemicals.

The following examples are intended only to further illustrate the invention and are not intended to limit the scope of the invention which is defined by the claims.

TABLE I

| Insecticides | | | |
|---|---|---|---|
| allethrin | −/+ | parathion | + |
| carbofuran | −/+ | primiphos methyl | + |
| diazinon | + | rotenone | −/+ |
| malathion | + | triphenyl phosphate | − |
| Herbicides | | | |
| 2,4-D | + | glyphosate | + |
| dinoseb | | | |
| Mycotoxins | | | |
| citrinin | + | ochratoxin A | + |
| deoxynivalenol | + | sterigmatocystin | + |
| griseofulvin | − | zearalenone | −/+ |
| mycophenolic acid | + | | |

TABLE I-continued

| Flavonoids | | | |
|---|---|---|---|
| hesperidin | − | quercetin | + |
| morin | + | rutin | + |
| naringin | + | 4',5,7-trihydroxyflavone | + |
| phloretin | + | umbelliferone | − |
| phloridzin dihydrate | + | | |
| Aromatic acids | | | |
| caffeic acid | + | ellagic acid | −/+ |
| trans-cinnamic acid | + | gallic acid | + |
| chlorogenic acid | + | tannic acid | + |
| Aromatic alcohols | | | |
| catechol | −/+ | phenol | + |
| cresol | + | resorcinol | −/+ |
| Plant toxins and meal contaminants | | | |
| amygdalin | + | raffinose | −/+ |
| jojoba (meal) | + | sinigrin | −/+ |
| phytic acid | + | stachyose | + |
| Other | | | |
| control | − | sucrose | + |

− = No growth detected
−/+ = Variable
+ = Growth detected

EXAMPLE 1

Yeast Isolation and Culture

The symbiont cultures were isolated using standard techniques [van der Walt, supra]. Fourth instar larvae of *L. serricorne* were surface sterilized in ethanol for 1 min and dissected under sterile conditions. Mycetome tissues were rinsed with two changes of sterile water and crushed onto malt extract agar. Morphology of the cultured organism was identical to that of prior reports [e.g., van der Walt, supra]. Yeast cultures were maintained at 25° C. on potato dextrose agar (PDA) and transferred monthly.

EXAMPLE 2

Carbon Sources Utilized by the Yeast

The xenobiotics listed in Table I were weighed out under sterile conditions and added to still-liquid Czapek's agar that had no other carbon source added. The concentration of chemicals was either 1% or 0.1%. Sucrose was the carbon source control. The absolute control had no carbon source. Slants were inoculated with 1- to 2-week-old yeast cultures (described in Example 1) by touching to colonies until a visible inoculum was present on the loop. A series of tubes were inoculated with the same loop to obtain diminishing doses of inoculum. Since the exact growth requirements of symbionts are not known, the standard method is to use a relatively heavy inoculum to supply micronutrients. Tubes were visually inspected weekly for growth for up to 2 months at 25° C. No growth occurred on tubes without a carbon source. Those tubes showing any fungal contamination (less than 1% of total) were eliminated from consideration. Cultures were also spot checked for bacterial contamination. Contamination was rare; and where it did occur, it made up a decidedly minor proportion of organisms present ($<0.01\%$), with the exception of jojoba meal. In a separate experiment, tubes were left uninoculated at 25° C. and examined for contamination after 1-2 weeks to test for the potential presence of microorganisms in the chemicals; only jojoba meal showed any contamination. Xenobiotic utilization is reported in Table I.

EXAMPLE 3

Esterase Activity of the Yeast

The xenobiotics listed in Table II were weighed (20 mg each) under sterile conditions, added to sterile tubes ($10\times 75$ mm), and dissolved in 500 $\mu$l ethanol. The solutions were added to 20 ml of sterile liquid PDA in $25\times 150$ mm tubes, blended with a vortex mixer, and dispensed into 9-cm petri plates. When the media had cooled to room temperature, they were streak-inoculated with about ¼ loopful of 1- to 2-week-old symbiont cultures (described in Example 1). After about 4 weeks at 25° C., 2 cm of colony growth was scraped from each of the plates and suspended in 2 ml of 0.1M phosphate buffer at pH 7.4. Then, 0.25 ml of this suspension was diluted 1:10 using the same buffer. Absorbance at 800 rm was determined, and the concentration of symbionts was adjusted to about 1 AU for assay by the spectrophotometric method of Dowd et al. [Pestic. Biochem. Physiol. 21: 275-282 (1984)], which measures 1-napthyl acetate hydrolase activity. The esterase activity induced by xenobiotics is reported in Table II. Because hydrolase activity was increased by the solvent, activity values are expressed as percentage of solvent control.

EXAMPLE 4

Replicate, 400-$\mu$l suspensions of NRRL Y-18546 (1.27 AU) in 0.1M phosphate buffer at pH 7.4 were incubated with 14,000 cpm ($1\times 10^{-5}$M) of radiolabeled parathion. After 1 hr at 30° C., the yeast was removed by centrifugation, and the supernatants were chromatographed on Whatman LK5DF plates and quantitated by liquid scintillation counting. Approximately 100 pmole of 4-nitrophenol was found, indicating that about 2.4% of the parathion had been hydrolyzed.

TABLE II

| Xenobiotics (0.1%) | Specific activity (nmole/min/AU) | Solvent Control (%) |
|---|---|---|
| control (no solvent) | 0.850 ± 0.015 | 89.5** |
| solvent control (SC) | 0.950 ± 0.013 | 100.0 |
| flavone | 1.750 ± 0.038 | 184.2** |
| griseofulvin | 1.100 ± 0.048 | 115.8** |
| cis(−)-β-pinene | 1.058 ± 0.025 | 111.4* |
| malathion | 1.083 ± 0.042 | 114.0* |

* = Value significantly different ($p < 0.05$) from the solvent control by analysis of variance.
** = Value highly significantly different ($p < 0.01$) from the solvent control by analysis of variance.

It is understood that the foregoing detailed description is given merely by way of illustration and that modifications and variations may be made therein without departing from the spirit and scope of the invention.

We claim:

1. A biologically pure culture of the yeast strain NRRL Y-18546 or subcultures thereof.

* * * * *